United States Patent
Jegou et al.

(10) Patent No.: US 10,646,428 B2
(45) Date of Patent: May 12, 2020

(54) PROCESS FOR COSMETIC TREATMENT OF KERATIN MATERIALS

(71) Applicant: L'OREAL, Paris (FR)

(72) Inventors: Gwenaëlle Jegou, Aulnay-sous-Bois (FR); Philippe Barbarat, Saint Ouen (FR); Gérard Malle, Villiers s/Morin (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/775,583

(22) PCT Filed: Nov. 28, 2016

(86) PCT No.: PCT/EP2016/078992
§ 371 (c)(1),
(2) Date: May 11, 2018

(87) PCT Pub. No.: WO2017/093183
PCT Pub. Date: Jun. 8, 2017

(65) Prior Publication Data
US 2018/0344617 A1     Dec. 6, 2018

(30) Foreign Application Priority Data

Nov. 30, 2015  (FR) ...................................... 15 61536

(51) Int. Cl.
| | | |
|---|---|---|
| *A61K 8/81* | (2006.01) | |
| *A61K 8/898* | (2006.01) | |
| *A61Q 1/00* | (2006.01) | |
| *A61K 8/49* | (2006.01) | |
| *A61Q 5/06* | (2006.01) | |
| *A61Q 5/12* | (2006.01) | |
| *A61K 8/86* | (2006.01) | |
| *A61Q 5/00* | (2006.01) | |

(52) U.S. Cl.
CPC .......... *A61K 8/8152* (2013.01); *A61K 8/4913* (2013.01); *A61K 8/4973* (2013.01); *A61K 8/8158* (2013.01); *A61K 8/8182* (2013.01); *A61K 8/86* (2013.01); *A61K 8/898* (2013.01); *A61Q 1/00* (2013.01); *A61Q 5/00* (2013.01); *A61Q 5/06* (2013.01); *A61Q 5/12* (2013.01); *A61K 2800/884* (2013.01); *A61K 2800/95* (2013.01)

(58) Field of Classification Search
None
See application file for complete search history.

(56) References Cited

U.S. PATENT DOCUMENTS

2008/0014154 A1   1/2008  Mougin et al.
2015/0037270 A1   2/2015  Pressly et al.

FOREIGN PATENT DOCUMENTS

| EP | 0 357 110 A1 | 8/1990 |
| FR | 2 872 514 A1 | 1/2006 |
| FR | 2 927 902 A1 | 8/2009 |
| FR | 2 962 034 A1 | 1/2012 |

OTHER PUBLICATIONS

Gandini, "The application of the diels-alder reaction to polymer syntheses based on furan/maleimide reversible couplings", Polimeros: Ciencia e Tecnologia, vol. 15, No. 2, pp. 95-101, 2005.

*Primary Examiner* — Jennifer A Berrios
(74) *Attorney, Agent, or Firm* — Polsinelli PC

(57) ABSTRACT

The invention relates to a cosmetic treatment process, in particular for caring for or making up keratin materials, comprising the following steps: a) a step of applying, to the keratin materials, a cosmetic composition comprising a compound comprising at least 2 maleimide groups; b) a step of applying a cosmetic composition comprising a compound comprising at least 2 furfuryl groups. The invention also relates to a kit comprising the two compositions, enabling said process to be carried out. The invention also relates to copolymers furfuryl (meth)acrylate, specifically (meth)acrylamide, and addition monomer chosen from polyethylene glycol (meth)acrylates and polydimethylsiloxanes with mono(meth)acryloyloxy end group.

26 Claims, No Drawings

PROCESS FOR COSMETIC TREATMENT OF KERATIN MATERIALS

CROSS REFERENCE TO RELATED APPLICATIONS

This application is a National Phase filing under 35 U.S.C. § 371 of PCT/EP2016/078992 filed on Nov. 28, 2016; and this application claims priority to Application No. 1561536 filed in France on Nov. 30, 2015 under 35 U.S.C. § 119. The entire contents of each application are hereby incorporated by reference.

The present invention relates to a process for the cosmetic treatment of human keratin materials, comprising the application, to the keratin materials, of a compound with furfuryl groups and a compound with maleimide groups. It also relates to a kit for carrying out such a process.

Film-forming polymers are commonly used in cosmetic products, in particular for hair styling, in make-up products and also in skincare products. The polymer film deposited on the keratin materials gives the cosmetic properties sought for these products.

Products are also sought which make it possible to form film-forming deposits in situ during the application thereof to the keratin materials. The advantage of such products is the ability to alter the form of the film-forming deposit over the whole time period of formation of this deposit.

The aim of the present invention is therefore to propose a process for the cosmetic treatment of keratin materials, making it possible to form a film in situ on keratin materials having good cosmetic properties, while avoiding the use of catalyst and the formation of undesirable by-products.

Another aim of the present invention is to propose a process making it possible to form a film in situ on keratin materials under standard conditions for the use of cosmetic products.

The inventors have discovered that such a process could be carried out using a compound with maleimide group and a compound with furfuryl groups.

Thus, a subject of the invention is a process for the cosmetic treatment of keratin materials, comprising the following steps:

a) a step of applying, to the keratin materials, a first, especially cosmetic, composition comprising a compound comprising at least 2 maleimide groups;

b) a step of applying a second, especially cosmetic, composition comprising a compound comprising at least 2 furfuryl groups.

The treatment process is in particular a cosmetic process for caring for or making up keratin materials. The cosmetic process is a non-therapeutic process.

Keratin materials mean the skin, lips, hair, eyelashes, nails, in particular of humans.

Advantageously, the process is applied to the skin and/or the hair.

Another subject of the invention is a kit comprising:

a first cosmetic composition containing a compound comprising at least 2 maleimide groups as defined below and a second cosmetic composition containing a compound comprising at least 2 furfuryl groups as defined below, the first and second compositions each being packaged in a separate packaging assembly.

The composition packaging assembly is, in a known manner, any packaging that is suitable for storing cosmetic compositions (especially a bottle, tube, spray bottle or aerosol bottle).

Such a kit makes it possible to carry out the process for treating keratin materials according to the invention.

In each part of the kit, the compound with maleimide group on the one hand and the compound with furfuryl group on the other are easy to use in a cosmetic composition without causing problems of viscosity of the composition containing same.

In the process according to the invention, the compound with maleimide groups and the compound with furfuryl groups react with one another according to the known Diels-Alder reaction to form a crosslinked material during the application of the compounds to keratin materials. The crosslinked material forms a deposit well-suited to the keratin materials.

The process according to the invention therefore makes it possible to form a film in situ on keratin materials which has good cosmetic properties. The film is transparent, has a non-tacky feel, and good water and shampoo resistance.

When the process is carried out on the hair, it makes it possible to obtain good hair shaping or styling. It is possible to alter the shaping of the hair in a similar way to a styling gel, until the compounds used in the process have completely crosslinked. In addition, the treated hair has good disentangling properties, both on wet hair and on dry hair.

When the process is carried out on the skin, it makes it possible to obtain a transparent film-forming deposit on the skin which is persistent with water and shampoo.

The treatment process is not aggressive for the keratin materials since the material resulting from the reaction of the compound with maleimide groups with the compound with furfuryl groups is formed without chemical catalyst.

The reaction between the compound with maleimide groups and the compound with furfuryl groups may be carried out at room temperature, especially at a temperature of between 10 and 50° C. It may also be carried out with a heating step, especially between 50 and 120° C., for example by means of a hairdryer or a hood. The heating step is generally suitable for a process for treating hair.

The reaction between the compound with maleimide groups and the compound with furfuryl groups may also be carried out with a step of application of light radiation (UV, etc.).

In a first embodiment of the process according to the invention, the process is performed by carrying out, in order, step a) (first step) then step b) (second step) described above.

In a second embodiment, the process is performed by carrying out, in order, step b) (first step) then step a) (second step) described above.

The composition containing the compound with furfuryl groups or the compound with maleimide groups having the highest molecular weight is preferably applied in the first step, then in the second step the composition containing the compound with furfuryl groups or the compound with maleimide groups having the lowest molecular weight is applied.

The second step is advantageously carried out in a period of time which may range from 1 second to 1 hour after having carried out the first step.

According to another embodiment of the process according to the invention, the first and second compositions may be extemporaneously mixed, then the mixture obtained may be applied to the keratin materials in a period of time of less than or equal to approximately 30 minutes after formation of the mixture.

Maleimide Compound

The process according to the invention uses a first cosmetic composition comprising a compound having at least two maleimide groups.

The maleimide group has the formula:

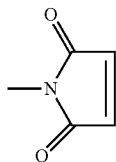

The compound with maleimide groups may be a compound of formula (I):

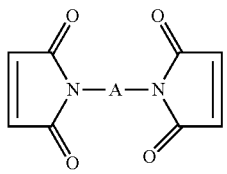

in which A denotes:

(i) a divalent hydrocarbon-based radical having from 3 to 20 carbon atoms, optionally substituted by one or more hydroxyl groups or by a maleimide group, optionally interrupted by an oxygen or sulfur atom or an —NR— group, R denoting a hydrogen atom or a $C_1$-$C_4$ alkyl radical or a —S(O)— or —$SO_2$— group or (ii) a polyethylene glycol and/or polypropylene glycol polymer chain; or (iii) a silicone polymer chain, in particular polydimethylsiloxane.

When A denotes a divalent hydrocarbon-based radical, the latter preferably has 3 to 6 carbon atoms, such as a propylene, butylene, pentylene or hexylene radical, optionally substituted with one or more hydroxyl groups. A is preferably a butylene radical or —$CH_2$—CH(OH)—CH(OH)—$CH_2$—.

As compound of formula (I), for which A denotes a divalent hydrocarbon-based radical as defined above, mention may be made of:

1,2-bis(maleimido)ethane, 1,3-bis(maleimido)propane, 1,4-bis(maleimido)butane, 1,5-bis(maleimido)pentane, 1,5-bis(maleimido)-2-methylpentane, 1,6-bis(maleimido) hexane, 1,7-bis(maleimido)heptane, 1,8-bis(maleimido)octane, 1,10-bis(maleimido)decane, 1,4-bis(maleimido)-2,3-butanediol, bis(N-maleimidomethyl) ether, 1,11-bis (maleimido)tetraethyleneglycol, 1,8-bis(maleimido triethyleneglycol, dithiobis(maleimido)ethane, 1,13-bis(maleimido)-4,7,10-trioxatridecane, 1,1'-(3,6,9,12-tetraoxatetradecane-1,14-diyl)bis(1H-pyrrole-2,5-dione), 1,2-bis(maleimido)benzene, 1,3-bis(maleimido)benzene, 1,4-bis (maleimido)benzene, 2,4-bis(maleimido)toluene, 4,4'-bis (maleimido)diphenylmethane, 4,4'-bis(maleimido)-1,1'-biphenyl, 1,1'-[methylenebis(2-ethyl-6-methyl-4,1-phenylene)]bismaleimide, 2,2-bis[4-(4-maleimidophenoxy) phenyl] propane, 4,4'-bis(maleimido)diphenyl ether, 1,4-bis (4-maleimidophenoxy)benzene, 1,3-bis(4-maleimidophenoxy)benzene, 1,1'-[methylenebis(6-methoxy-3,1-phenylene)]bis 1H-pyrrole-2,5-dione, 1,1'-[1,4-phenylenebis[(1-oxo-2-propene-3,1-diyl)-3,1-phenylene]] bis-1H-pyrrole-2,5-dione, 4,4'-diphenyl sulfide bismaleimide, bis[4-maleimido(4-phenoxyphenyl)] sulfone bis-(1,13-(3-malemidopropionyl)amido)-4,7,10-trioxatridecane tris(2-maleimidoehyl)amine.

As compound of formula (I) for which A denotes a polyethylene glycol and/or polypropylene glycol polymer chain as defined above, mention may be made of the polyethylene glycol bis(maleimides), especially those of formula (Ia):

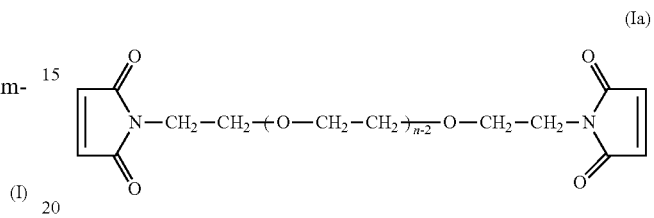

in which n is between 30 and 300, preferably between 30 and 100, and preferentially from 30 to 60.

Polyethylene glycol bis(maleimides) are especially sold under the names P2MAL-10, P2MAL-8, P2MAL-6, P2MAL-3, P2MAL2 by SUNBIO. They respectively have a polyethylene glycol chain of molecular weight of 10 K (i.e. n approximately 225), 8 K (i.e. n approximately 180), 6K (i.e. n approximately 135), 3.4K (i.e. n approximately 76), 2K (i.e. n approximately 45).

It is also possible to use polymers containing more than two maleimide groups, such as, for example:

the tetrafunctional polymer pentaerythritol tetra{[3-(3-maleimido-1-oxopropyl)amino] propyl}polyoxyethylene in which each polyoxyethylene segment comprises from 4 to 500 ethylene oxide units the maleimidoalkylmethylsiloxane-dimethylsiloxane copolymers of formula (II)

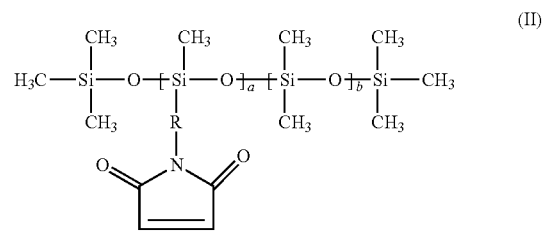

in which R denotes a divalent hydrocarbon-based radical having from 1 to 15 carbon atoms, optionally interrupted by one or more non-adjacent oxygen atom(s) or —NR'— groups, R' denoting H or a $C_1$-$C_4$ alkyl group;

a is a number ranging from 1 to 50, preferably ranging from 1 to 10, b is a number ranging from 10 to 400, preferably ranging from 30 to 75, R advantageously denotes a divalent hydrocarbon-based radical having from 2 to 6 carbon atoms; a ranges from 1 to 10 and b ranges from 30 to 75.

polymers of formula (III):

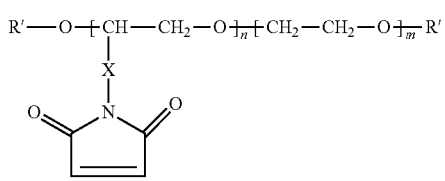

in which:
R' denotes a hydrogen atom or a $C_1$-$C_3$ alkyl group,
X denotes a divalent $C_1$-$C_{15}$ hydrocarbon-based group, optionally interrupted by one or more non-adjacent oxygen atom(s) or —NR'— groups, R' denoting H or a $C_1$-$C_4$ alkyl group;
n is a number ranging from 1 to 20, preferably ranging from 3 to 12,
m+n is a number ranging from 3 to 3000,
the polymers of formula (IV):

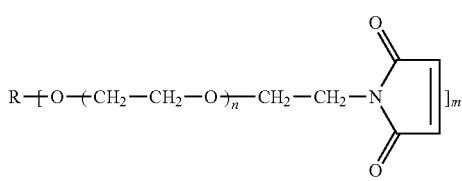

in which:
R denotes a multivalent radical derived from a $C_3$-$C_{12}$ polyol, in particular from sorbitol or from pentaerythritol
n is an integer ranging from 3 to 3000,
m is an integer ranging from 3 to 12.
Polymers (III) and (IV) are especially described in document U.S. Pat. No. 6,828,401.
The compound with maleimide groups is preferably chosen from:
compounds of formula (I) for which A denotes a divalent radical having from 3 to 6 carbon atoms, optionally substituted by one or more hydroxyl groups;
compounds of formula (Ia) for which n is between 30 and 100;
compounds of formula (II) for which R denotes a divalent hydrocarbon-based radical having from 2 to 6 carbon atoms; a ranges from 1 to 10 and b ranges from 30 to 75.
The compound with maleimide groups is more preferentially chosen from:
1,4-bis(maleimido)-2,3-butanediol;
compounds of formula (Ia) for which n is between 30 and 60;
compounds of formula (II) for which R denotes a divalent propylene radical, a ranges from 2 to 5 and b ranges from 40 to 70.
The compound with maleimide groups may be present in the first composition in a content ranging from 0.1% to 40% by weight, preferably ranging from 0.5% to 20% by weight and preferentially ranging from 0.5% to 15% by weight, relative to the total weight of the composition.
Furfuryl Compound:
The process according to the invention uses a second cosmetic composition comprising a compound with furfuryl groups (having 2 ethylenic unsaturations).

The compound with furfuryl groups may be a compound of formula (V):

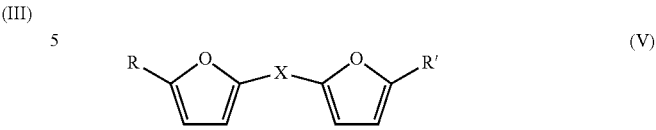

in which:
X denotes:
(i) a divalent —C($R_1$)($R_2$)— group, with $R_1$ and $R_2$ denoting a $C_1$-$C_4$ alkyl radical; or
R1=H and $R_2$ denotes a $C_1$-$C_4$ alkyl group, or —OH or $NHR_3$, with $R_3$=$C_1$-$C_4$ alkyl radical;
(ii) a sulfur atom;
(iii) a —CO— group;
(iv) an —Si($R_4$)($R_5$) group, $R_4$ and $R_5$ denoting a $C_1$-$C_4$ alkyl radical,
R and R' denote a $C_1$-$C_4$ alkyl radical or a —CHO aldehyde group.
As furfuryl compound (V), mention may be made of:
bis(2-furylmethoxy)(dimethyl)silane
di-2-furanyl methanone
bis-furan-2,2'-(1-methylethylidene)
bis(5-methyl-2-furyl) ketone
alpha-2-furanyl-2-furanemethanamine
5,5'-thiobis 2-furan carboxaldehyde
alpha-2-furanyl-2-furanmethanol
5,5'-(1-Methylethylidene)bis-2-furan carboxaldehyde
N-ethyl-5-methyl-alpha-(5-methyl-2-furanyl)-2-furanmethanamine
2,2"methylene bis-furan
di-2-furanyldimethyl silane.
The furfuryl compound (V) is preferably bis(2-furylmethoxy)(dimethyl)silane.
The compound with furfuryl groups may also be a polymer with furfuryl groups. As examples of such polymers, mention may be made of:
copolymers of 4-furfuryloxymethylstyrene and styrene, such as those described in the article "Synthesis of Organic-Inorganic Polymer Hybrids Controlled by Diels-Alder Reaction", Adachi et al, Macromolecules (2004), 37(26), 9793-9797.
furan-modified poly(2-methyl-2-oxazolines) such as those described in the article "Thermally Reversible IPN Organic-Inorganic Polymer Hybrids Utilizing the Diels-Alder Reaction", Imai et al, Macromolecules (2000), 33(12), 4343-4346
furan-modified poly(N-acetylethylenimines) such as those described in the article "Reversible gelation of polyoxazoline by means of Diels-Alder reaction" Chujo et al, Macromolecules (1990), 23(10), 2636-41.
copolymers of furfuryl methacrylate and styrene, such as those described in the articles "Some observations on the copolymerization of styrene with furfuryl methacrylate», Goiti et al, Polymer 2001, 42, 10187 and "Thermal breakdown by the retro Diels-Alder reaction of crosslinking in poly(styrene-co-furfuryl methacrylate)", Goiti et al, Macromolecular Rapid Communications 2003, 24, 692.
polyamides with furan function, such as those described in the publication "Recent Advances in Environmentally Compatible Polymers: Cellucon '99 Proceedings» by Kennedy et al (ISBN: 978-1-85573-545-3), page 28 copolymers of furfuryl (meth)acrylate, (meth)acrylamide and additional monomer as defined below (copolymer resulting from the polymerization of these monomers):

i) the furfuryl (meth)acrylate is preferably furfuryl methacrylate.

The furfuryl (meth)acrylate may be present in a content ranging from 0.1% to 40% by weight, especially ranging from 0.2% to 25% by weight, preferably ranging from 0.5% to 15% by weight, relative to the weight of the final polymer.

ii) (meth)acrylamides of formula $CH_2=C(R1)-CONR'_3R'_4$, in which:

R1 denotes H or methyl;

R'3 and R'4, which are identical or different, represent a hydrogen atom or a linear or branched alkyl group comprising from 1 to 6 carbon atoms, which may comprise one or more substituents chosen from —OH, =O, halogen atoms (F, Cl, Br or I) and —NR'R" with R' and R", which are identical or different, chosen from linear or branched C1-C4 alkyls; or R'3 represents a hydrogen atom and R'4 represents a 1,1-dimethyl-3-oxobutyl group;

By way of examples of alkyl groups that may constitute R'3 and R'4, mention may be made of n-butyl, t-butyl, n-propyl, dimethylaminoethyl, diethylaminoethyl and dimethylaminopropyl.

As monomer, mention may be made of dimethylaminopropyl methacrylamide; acrylamide, methacrylamide, N-tert-butylacrylamide, diacetone acrylamide of formula $CH_2=CH-C(O)NHC(CH_3)_2-CH_2-C(O)CH_3$;

iii) the additional monomer is chosen from:

a) the monomers of formula (VI), alone or as a mixture:

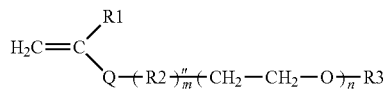

(VI)

in which:

$R_1$ is a hydrogen atom or a methyl radical;

Q is a divalent group chosen from —COO—, —CONH—, $R_2$ is a saturated or unsaturated, optionally aromatic, linear, branched or cyclic divalent carbon-based radical comprising 1 to 18 carbon atoms, which may comprise 1 to 4 non-adjacent heteroatoms chosen from O, S or an —NR'— group, R' denoting H or a C1-C4 alkyl group, m is 0 or 1 n is an integer between 65 and 700;

$R_3$ is a hydrogen atom or a linear, branched or cyclic, saturated or unsaturated, optionally aromatic carbon-based radical, comprising 1 to 30 carbon atoms, which may comprise 1 to 4 non-adjacent heteroatoms chosen from O or S or an —NR'— group, R' denoting H or a $C_1$-$C_4$ alkyl group, In the radical $R_2$, the heteroatom(s), when present, may be inserted in the chain of said radical $R_2$, or else said radical $R_2$ may be substituted by one or more groups comprising same, such as OH, SH or amino (NR'R", with R', R", which are identical or different, representing a hydrogen or a linear or branched $C_1$-$C_4$ alkyl, especially methyl or ethyl).

$R_2$ may especially be:

a $C_1$-$C_{18}$ alkylene radical such as methylene, ethylene, propylene, n-butylene, isobutylene, tert-butylene, n-hexylene, n-octylene, n-dodecylene, n-octadecylene, n-tetradecylene, n-docosanylene, optionally substituted by OH, NR'R";

a —$C_6H_4$— (ortho, meta or para) phenylene radical, optionally substituted by a $C_1$-$C_{12}$ alkyl;

a —$C_6H_4$—$CH_2$ benzylene radical, optionally substituted by a $C_1$-$C_{10}$ alkyl;

a linear or branched divalent $C_1$-$C_{12}$ alkyleneoxy radical, for example —$CH_2$—$CH_2$—$CH_2$—O— (propyloxy).

$R_2$ is preferentially a linear $C_1$-$C_6$ alkylene radical.

n is preferably between 75 and 500, better still between 80 and 400, or even between 90 and 300, and preferentially between 95 and 250, even better still between 100 and 200.

$R_3$ is preferably a hydrogen atom; a benzyl radical; a phenyl radical optionally substituted by a $C_1$-$C_{12}$ alkyl, a $C_1$-$C_{30}$, especially $C_1$-$C_{22}$, or even $C_2$-$C_{16}$ alkyl radical, optionally comprising 1 to 4 non-adjacent heteroatoms chosen from O, S or an —NR'— group, R' denoting H or a $C_1$-$C_4$ alkyl group. Mention may especially be made of the methyl, ethyl, propyl, benzyl, ethylhexyl, lauryl, stearyl or behenyl radicals.

Among the preferred monomers of formula (VI), mention may be made of:

poly(ethylene glycol) (meth)acrylate in which $R_1$ is H or methyl; Q is COO, m=0 and $R_3$=H;

methylpoly(ethylene glycol) (meth)acrylate, also known as methoxypoly(ethylene glycol) (meth)acrylate, in which $R_1$ is H or methyl; Q is COO, m=0 and $R_3$=methyl, poly(ethylene glycol) (meth)acrylates in which $R_1$ is H or methyl; Q is COO, m=0 and $R_3$=alkyl;

phenylpoly(ethylene glycol) (meth)acrylates, also known as poly(ethylene glycol) (meth)acrylate phenyl ether, in which $R_1$ is H or methyl; Q is COO, m=0 and $R_3$=phenyl.

The most particularly preferred monomers of formula (VI) are chosen from poly(ethylene glycol) (meth)acrylates and methylpoly(ethylene glycol) (meth)acrylates, preferably those having a weight-average molecular weight of between 2800 and 30 000 g/mol, especially between 3500 and 20 000 g/mol, or even between 4000 and 10 000 g/mol.

Examples of commercial monomers are:

polyethylene glycol 8000 or 4000 methacrylates from Monomer & Polymer Dajac Laboratories;

methoxypoly(ethylene glycol) methacrylates with MW ranging from 750 to 5005, available from EVONIK under the trade names VISIOMER® MPEG-500-MA; VISIOMER® MPEG-1005-MA; VISIOMER® MPEG-2005-MA W the methoxypoly(ethylene glycol) methacrylates 5K, 10K, 12K, 20K and 30K from Sunbio.

b) a polydimethylsiloxane monomer with mono(meth)acryloyloxy end group of the following formula (VII) (referred to hereinafter as silicone macromonomer):

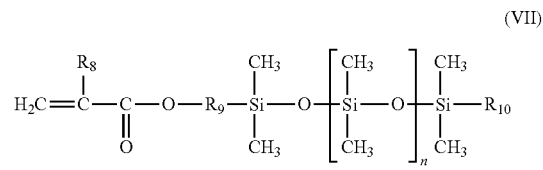

(VII)

in which:

$R_8$ denotes a hydrogen atom or a methyl group; preferably methyl;

R$_9$ denotes a linear or branched, preferably linear, divalent hydrocarbon-based group having from 1 to 10 carbon atoms, preferably having from 2 to 4 carbon atoms, and optionally containing one or two —O— ether bonds; preferably an ethylene, propylene or butylene group;

R$_{10}$ denotes a linear or branched alkyl group having from 1 to 10 carbon atoms, especially from 2 to 8 carbon atoms; preferably methyl, ethyl, propyl, butyl or pentyl;

n denotes an integer ranging from 1 to 300, preferably ranging from 3 to 200 and preferentially ranging from 5 to 100.

Use may in particular be made of monomethacryloyloxypropyl polydimethylsiloxanes such as those sold under the names MCR-M07, MCR-M17, MCR-M11 and MCR-M22 by Gelest Inc or X-22-2475, X-22-2426 and X-22-174DX by Shin Etsu.

(iii) and optionally an alkyl (meth)acrylate chosen from:

(a) linear or branched, saturated or unsaturated C$_1$-C$_{20}$ alkyl (meth)acrylates, optionally interrupted by one or more non-adjacent heteroatoms chosen from O or S or by an NR group, R being a C1-C4 alkyl group, optionally substituted by a phenyl or furfuryl group;

(b) saturated C$_4$-C$_8$ cycloalkyl (meth)acrylates optionally interrupted by O or NH.

Particularly preferred copolymers of furfuryl (meth)acrylate, (meth)acrylamide and additional monomer are copolymers of:

i) furfuryl methacrylate;

ii) (meth)acrylamide of formula CH$_2$=C(R1)—CONR'$_3$R'$_4$, in which:

R1 denotes H or methyl;

R'$_3$ and R'$_4$, which are identical or different, represent a hydrogen atom or a linear or branched alkyl group comprising from 1 to 6 carbon atoms, which may comprise an —NR'R" substituent, with R' and R", which are identical or different, chosen from linear or branched C$_1$-C$_4$ alkyls;

in particular, said (meth)acrylamide is dimethylaminopropyl methacrylamide iii) additional monomer chosen from:

a) the monomers of formula (VI'), alone or as a mixture:

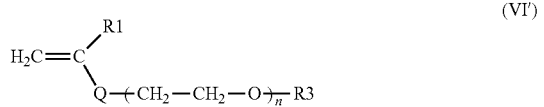

(VI')

in which:
R$_1$ is a hydrogen atom or a methyl radical;
Q is a divalent group —COO—,
n is an integer between 65 and 700;
R$_3$ is a hydrogen atom or a methyl radical
n is preferably between 75 and 500, better still between 80 and 400, or even between 90 and 300, and preferentially between 95 and 250, even better still between 100 and 200.

b) a polydimethylsiloxane monomer with mono(meth)acryloyloxy end group of the following formula (VII'):

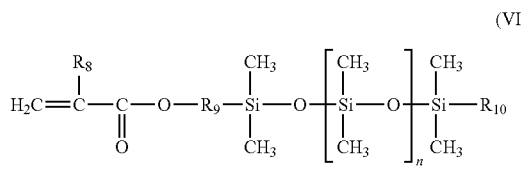

(VII')

in which:
R$_8$ denotes a hydrogen atom or a methyl group; preferably methyl;
R$_9$ denotes a linear divalent hydrocarbon-based group having from 2 to 4 carbon atoms;
R$_{10}$ denotes an alkyl group chosen from methyl, ethyl, propyl, butyl or pentyl;
n denotes an integer ranging from 1 to 300, preferably ranging from 3 to 200 and preferentially ranging from 5 to 100.

iv) and optionally a C$_1$-C$_{20}$ alkyl (meth)acrylate monomer.

The furfuryl copolymer described above may be obtained from said monomers in the following contents (by weight relative to the total weight of monomers used):

furfuryl (meth)acrylate: from 1% to 50% by weight, preferably ranging from 5% to 45% by weight.

(meth)acrylamide: from 1% to 90% by weight, preferably ranging from 5% to 50% by weight.

Additional monomer (VI), (VI') or (VII), (VII'): from 1% to 90% by weight, preferably ranging from 5% to 50% by weight.

alkyl (meth)acrylate if present: from 1% to 90% by weight, preferably ranging from 5% to 50% by weight.

When the furfuryl copolymer comprises a monomer of (meth)acrylamide type with at least one —NR'R" group as defined above, said copolymer may be neutralized by a neutralizing agent of inorganic or organic acid type.

As example of inorganic acid, mention may be made of sulfuric acid, hydrochloric acid, hydrobromic acid, hydriodic acid, phosphoric acid and boric acid. Hydrochloric acid is preferably used.

As example of organic acid, mention may be made of:

Mention may be made especially of propionic acid, acetic acid, terephthalic acid, citric acid and tartaric acid.

Linear, branched or cyclic, saturated or unsaturated, optionally aromatic fatty acids having from 2 to 32 carbon atoms, especially 2 to 20, and comprising at least one COOH or sulfonic acid (—SO$_3$H) function.

Linear, branched or cyclic, saturated or unsaturated, optionally aromatic hydroxy acids, especially alpha-hydroxy acids having 3 to 32 and especially 3 to 20 carbon atoms, and comprising at least one COOH or sulfonic acid (—SO$_3$H) function, may also be used.

Alkylbenzenesulfonic acids in which the alkyl group may comprise from 4 to 30 and especially 6 to 24 carbon atoms may also be used.

Amphoteric neutralizing agents may also be used, especially of the alkylbetaine or alkylamidopropylbetaine type, in which the alkyl group may comprise 4 to 30, especially 6 to 24 carbon atoms; mention may be made in particular of cocamidopropylbetaine.

Mention may be made especially of alpha-hydroxyethanoic acid, alphahydroxyoctanoic acid, alpha-hydroxycaprylic acid, ascorbic acid, acetic acid, benzoic acid, behenic acid, capric acid, citric acid, caproic acid, caprylic acid, dodecylbenzenesulfonic acid, 2-ethylcaproic acid, folic acid, fumaric acid, galactaric acid, gluconic acid, glycolic acid, 2-hexadecyleicosanoic acid, hydroxycaproic acid, 12-hydroxystearic acid, isolauric (or 2-butyloctanoic) acid, isomyristic (or 2-hexyloctanoic) acid, isoarachidic (or 2-octyldodecanoic) acid, isolignoceric (or 2-decyltetradecanoic) acid, lactic acid, lauric acid, malic acid, myristic acid, oleic acid, palmitic acid, propionic acid, sebacic acid, stearic acid, tartaric acid, terephthalic acid, trimesic acid, undecylenic acid, propylbetaine, cocamidopropylbetaine and betaine hydrochloride of formula [(CH$_3$)3N+CH$_2$CO$_2$H.C$_1^-$], and also mixtures thereof.

Preferably, caproic acid, 2-ethylcaproic acid, oleic acid, behenic acid, stearic acid, acetic acid, citric acid, tartaric acid, betaine hydrochloride and/or gluconic acid, and preferentially betaine hydrochloride, may be used as neutralizing agent.

The neutralizing agent, alone or as a mixture, may be added in an amount of 0.01 to 3 molar equivalent, especially 0.05 to 2.5, or even 0.1 to 2 molar equivalent, relative to the total amine functions of the polymer or of the monomers.

The neutralizing agent, alone or as a mixture, is preferably present in a stoichiometric amount relative to the total amine functions of the polymer or monomers; it is therefore present in an amount necessary to neutralize 100% of the amine units of the polymer or of the monomers, i.e 1 molar equivalent.

The compound with furfuryl group is preferably chosen from the following polymers:

polyethylene glycol methacrylate/dimethylaminopropyl methacrylamide/furfuryl methacrylate copolymer (in particular in the weight ratio 45/45/10), especially neutralized with betaine hydrochloride;

2-ethylhexyl/dimethylaminopropyl methacrylamide/furfuryl methacrylate/PDMS acrylate copolymer (in particular in the weight ratio 30/30/20/20)

2-ethylhexyl/furfuryl methacrylate/PDMS acrylate copolymer (in particular in the weight ratio 40/40/20) the PDMS acrylate being of formula:

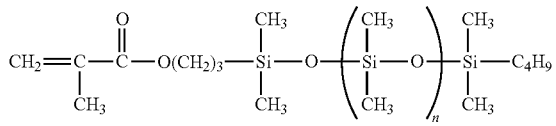

n being between 60 and 70.

These polymers may be prepared in a known way by optionally controlled free-radical polymerization technology. A polymerization process is illustrated in the examples.

Another subject of the invention, as novel compounds, is the copolymers of furfuryl (meth)acrylate, (meth)acrylamide and additional monomer and optionally alkyl (meth) acrylate as defined above.

Another subject of the invention is a composition comprising, in a physiologically acceptable medium, a copolymer of furfuryl (meth)acrylate, (meth)acrylamide, and additional monomer and optionally alkyl (meth)acrylate as defined above.

The compound with furfuryl groups may be present in the second composition in a content ranging from 0.1% to 30% by weight, preferably ranging from 0.5% to 20% by weight and preferentially ranging from 1% to 15% by weight, relative to the total weight of the composition.

According to a preferred embodiment of the process according to the invention, the compound with maleimide groups and the compound with furfuryl groups are used in amounts such that the mole ratio of the number of maleimide groups relative to the number of furfuryl groups is between 0.95 and 1.05, preferably between 0.98 and 1.02.

The cosmetic compositions used according to the invention contain a physiologically acceptable medium, that is to say a medium that is compatible with human keratin materials such as the skin (of the body, face, around the eyes or the scalp), the hair, the eyelashes, the eyebrows, bodily hair, the nails or the lips.

According to one embodiment of the invention, the first and/or second cosmetic composition used according to the invention may comprise a physiologically acceptable aqueous medium. It may be constituted, for example, of water or of a mixture of water and of at least one cosmetically acceptable organic solvent. By way of example of organic solvent, mention may be made of C$_2$-C$_4$ lower alcohols, such as ethanol and isopropanol; polyols, especially those having from 2 to 6 carbon atoms, for instance glycerol, propylene glycol, butylene glycol, pentylene glycol, hexylene glycol, dipropylene glycol or diethylene glycol; polyol ethers, for instance 2-butoxyethanol, propylene glycol monomethyl ether, diethylene glycol monomethyl ether or monoethyl ether, and short esters such as ethyl acetate or butyl acetate; and mixtures thereof.

According to another embodiment of the invention, the first and/or second cosmetic composition used according to the invention comprises a physiologically acceptable non-aqueous medium. It may be constituted, for example, by one or more cosmetically acceptable organic solvents, such as those described previously, or else one or more common cosmetic oils.

The non-aqueous medium preferably comprises a volatile oil.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and at atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

These volatile oils may be hydrocarbon-based oils or silicone oils, or mixtures thereof. The term "hydrocarbon-based oil" means an oil mainly containing hydrogen and carbon atoms and possibly oxygen, nitrogen, sulfur and/or phosphorus atoms.

The volatile hydrocarbon-based oils may be chosen from hydrocarbon-based oils having from 8 to 16 carbon atoms, and especially branched C$_8$-C$_{16}$ alkanes such as C$_8$-C$_{16}$ isoalkanes of petroleum origin (also known as isoparaffins), for instance isododecane (also known as 2,2,4,4,6-pentamethylheptane), isodecane, isohexadecane and, for example, the oils sold under the trade names Isopar® or Permethyl®.

Volatile silicone oils that may be mentioned include volatile linear or cyclic silicone oils, especially those with a viscosity ≤8 centistokes (cSt) (8×10$^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The compositions used according to the invention may also contain one or more cosmetic additives chosen from surfactants, sunscreens, fillers, colorants, nacreous agents, opacifiers, sequestrants, film-forming polymers, plasticizers, thickeners, oils, waxes, fragrances and preserving agents.

The compositions used according to the invention may be in any galenical form conventionally used and especially in the form of aqueous solutions, aqueous-alcoholic solutions, oil-in-water (O/W), water-in-oil (W/O) or multiple (triple: W/O/W or O/W/O) emulsions, aqueous gels or aqueous-alcoholic gels. These compositions are prepared according to the usual methods.

The invention is illustrated in greater detail in the examples that follow.

EXAMPLE 1: 2-ETHYLHEXYL ACRYLATE/DIMETHYLAMINOPROPYL METHACRYLAMIDE/FURFURYL METHACRYLATE/PDMS ACRYLATE*COPOLYMER (30/30/20/20)

100 g of methyl ethyl ketone were introduced into a four-necked flask on which is mounted a condenser and two dropping funnels, heating was carried out to 75° C., then 150 ml of a solution containing 50 g of methyl ethyl ketone and 30 g of 2-ethylhexyl acrylate, 30 g of dimethylaminopropyl methacrylamide (DMAPMA) and 20 g of furfuryl methacrylate and 20 g of polydimethylsiloxane acrylate (MCR 17 from Gelest*) were poured in dropwise over 30 minutes. In parallel, 50 g of methyl ethyl ketone with 1.5% tert-butyl peroxy-2-ethylhexanoate (Trigonox 21S from Akzo) are poured in. The mixture was left stirring for 5 hours. After cooling, 150 ml of dodecamethylpentasiloxane (D5) were introduced and the methyl ethyl ketone was evaporated.

A 24.7% AM solution of copolymer in D5 was obtained.
The structure of MCR 17 from Gelest is as follows:

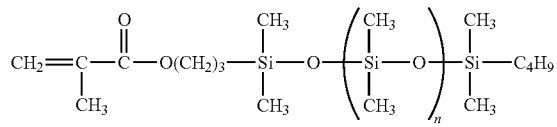

n being such that the molecular weight of the monomer is approximately 5000. i.e. n=approximately 65 (between 60 and 70)

EXAMPLE 2: POLYETHYLENE GLYCOL METHACRYLATE/DIMETHYLAMINOPROPYL METHACRYLAMIDE/FURFURYL METHACRYLATE COPOLYMER (45/45/10), TOTALLY NEUTRALIZED WITH BETAINE HYDROCHLORIDE (100% OF THE UNITS ORIGINATING FROM THE DIMETHYLAMINOPROPYL METHACRYLAMIDE ARE NEUTRALIZED)

80 ml of methyl ethyl ketone were introduced into a round-bottomed flask on which is mounted a condenser and a dropping funnel, heating was carried out for 30 minutes at 80° C., then 120 ml of a solution containing 18.5 g of methyl ethyl ketone with 45 g of dimethylaminopropyl methacrylamide (DMAPMA), 45 g of methoxy polyethylene glycol methacrylate (12 ethylene oxide units) (Bisomer® MPEG 550 MA from Cognis) and 10 g of furfuryl methacrylate and 1.5 g of tert-butyl peroxy-2-ethylhexanoate (Trigonox 21S from Akzo) were poured in dropwise in 45 minutes. The reaction mixture was left at 80° C. for 3 hours, then 0.5 g of Trigonox 21S were added. The mixture was left to heat for 2 additional hours at 80° C. before allowing it to cool to room temperature. The mixture was then introduced into a round-bottomed flask and then 40 g of betaine hydrochloride and 250 ml of water were added. The methyl ethyl ketone was evaporated and the polymer was obtained in solution in water at a concentration of 33% by weight.

EXAMPLE 3: DIMETHYLSILOXANE/MALEIMIDOPROPYLMETHYLSILOXANE COPOLYMER 100 g of dimethylsiloxane/aminopropylmethylsiloxane (AMS-162 from Gelest) copolymer (0.84 mol of amino group, 1 eq.) were added to 8.2 g of maleic anhydride (0.084 mol, 0.1 eq) in 500 ml of dichloromethane in a 1 litre round-bottomed flask. The reaction medium was stirred at room temperature for 1 hour then concentrated to dryness in a rotary evaporator under reduced pressure until an oil was obtained. The polymer obtained (0.84 mol) was then dissolved in 500 ml of methyl ethyl ketone and 11.3 g of triethylamine (0.084 mol, 0.13 eq). The medium was then heated to 80° C. and 8.5 g of acetic anhydride (0.084 mol, 0.1 eq) were added in 5 minutes. The reaction was continued at reflux with stirring for 14 hours. The reaction medium was then concentrated in a rotary evaporator under reduced pressure until a brown oil was obtained. The latter was dissolved in 200 ml of dichloromethane (2 V) then washed twice with 50 ml of distilled water (2×0.5 V). The organic phase was concentrated in a rotary evaporator until a viscous brown oil was obtained (yield: 94%).

EXAMPLE 4: DIMETHYLAMINOPROPYL METHACRYLAMIDE/METHOXYPOLY(ETHYLENE GLYCOL) 5000 METHACRYLATE/FURFURYL METHACRYLATE COPOLYMER (45/45/10), TOTALLY NEUTRALIZED WITH BETAINE HYDROCHLORIDE (100% OF THE UNITS ORIGINATING FROM THE DIMETHYLAMINOPROPYL METHACRYLAMIDE ARE NEUTRALIZED)

The copolymer according to the procedure of Example 2 was prepared, using:
45 g of dimethylaminopropyl methacrylamide (DMAPMA),
45 g of methoxypoly(ethylene glycol) 5000 methacrylate (Norsocryl 405® from Arkema),
10 g of furfuryl methacrylate,
1.5 g+0.5 g of tert-butyl peroxy-2-ethylhexanoate (Trigonox 21S from Akzo),
40 g of betaine hydrochloride
The polymer was obtained in solution in water at a concentration of 35% by weight.

EXAMPLE 5

A maleimide compound (A) was used, polyethylene glycol bis(maleimide) (reference: P2MAL-2 from Sunbio).
The following compositions were prepared:
Composition 1: aqueous solution containing 1% AM of polymer from example 2
Composition 2: aqueous solution containing 6% of compound (A)
Locks of sensitized hair (bleaching SA 20%), comprising 2.5 g of hair, were used.
Composition 1 and/or composition 2 were applied to the locks of hair according to the following protocols:
Lock 1: application of 75 mg of composition 1 (1% AM of polymer of example 2)

It was then left on for 30 minutes at room temperature. Composition 2 was then applied and left on for 30 minutes at 60° C. (under a hood).

Lock 2: protocol similar to that used for lock 1 but with inversion of the application of the compositions: composition 2 was applied first to the lock and then composition 1 was applied.

Lock 3: only composition 2 was applied

Lock 4: only composition 1 was applied

Lock 0: control lock, only treated with water in the same protocol.

After treating the lock, the following were evaluated:

Disentangling by combing the lock before (wet disentangling) and after drying (dry disentangling), grading from 0 to 10.

0: very difficult to disentangle

10: very easy to disentangle.

Each lock was then washed with a DOP camomile shampoo (LA SCAD) at an amount of 0.5 g of shampoo per 2.7 grams of hair, at a temperature of 38° C. Moisten the lock for 5 seconds with water. Apply the shampoo, massaging the lock from the root to the end for 15 seconds. Leave on for 3 minutes then rinse with water (10 passes under tap water for 10 seconds). Wring out. Dry the locks for 30 minutes at 60° C. with a drying hood.

The step of washing/drying the locks was repeated 10 times.

The disentangling properties were evaluated after the first, third, fifth and tenth washes.

The following results were obtained:

|  | Wet disentangling | Dry disentangling | Wet disentangling after 1 shampoo operation | Dry disentangling after 1 shampoo operation |
| --- | --- | --- | --- | --- |
| Lock 1 | 8 | 7 | 6 | 6 |
| Lock 2 | 7 | 7 | 6 | 6 |
| Lock 3 | 3 | 3 | 2 | 3 |
| Lock 4 | 5 | 4 | 2 | 3 |
| Lock 0 | 3 | 3 | 1 | 2 |

The results obtained show that locks 1 and 2 treated with the process according to the invention have very good disentangling (wet and dry) relative to the control lock 0 (only treated with water under the same conditions).

Locks 3 and 4 (not in accordance with the invention) have worse disentangling properties than those of locks 1 and 2.

EXAMPLE 6

The furfuryl compound (B), bis(2-furanylmethoxy)(dimethyl)silane (RN 3256-20-0) was used.

The following compositions were prepared:

Composition 3: solution containing 50% by weight of AM of polymer from example 3 in cyclopentasiloxane Composition 4: solution containing 40% by weight of AM of the furfuryl compound (B) in cyclopentasiloxane.

Locks of natural hair comprising 2.7 g of hair, were used.

Composition 3 and/or composition 4 were applied to the locks of hair according to the following protocols:

Lock 5: application of 5.4 g of composition 4 by spreading out with a brush, this was then left on for 30 minutes at room temperature and the locks were then wrung out.

Composition 4 was then applied by spreading out with a brush and was left on for 30 minutes.

The lock was then dried at 60° C. with a hairdryer for 5 minutes

The cosmetic properties of the lock were observed one hour later.

Lock 6: only composition 4 is applied

The visual appearance of the treated lock (styling appearance, stuck-together appearance of the lock) and the tacky feel thereof were then observed.

The following were evaluated:

The stuck-together appearance of the lock, grading:

++: very stuck-together lock

+: slightly stuck-together lock

−: lock not stuck together

The tacky appearance of the lock, grading:

−: non-tacky appearance

+: tacky appearance

The following results were obtained:

|  | Styling appearance | Stuck-together lock | Tacky appearance |
| --- | --- | --- | --- |
| Lock 6 | No | − | + |
| Lock 5 | Yes | ++ | − |

These results show that lock 5 treated with the process according to the invention makes it possible to obtain a styling effect and a lock which does not have a very tacky feel.

EXAMPLE 7

A maleimide compound (C), 1,4-bis(maleimido)-2,3-butanediol was used.

The following compositions were prepared:

Composition 5: solution containing 5% of polymer from example 1 in cyclopentasiloxane Composition 6: aqueous solution containing 2.5% by weight of maleimide compound (C)

Locks of natural Caucasian hair comprising 2.7 g of hair, were used.

Composition 5 and/or composition 6 were applied according to the following protocols:

Lock 7: application of 5.5 g of composition 5 by spreading out with a brush, this was then left on for 30 minutes at room temperature and the locks were then wrung out.

Composition 6 was then applied by spreading out with a brush and was left on for 30 minutes. The lock was then rolled on a roller then the rolled lock was dried with a hood at 50° C. for 30 minutes. The lock from the roller was unwound and the cosmetic properties of the treated lock were observed.

Lock 8: same protocol as that for lock 7, applying just composition 5.

Lock 9: same protocol as that for lock 7, applying just composition 6.

The curly appearance of the treated lock and the tacky feel thereof were then observed.

The following were evaluated:

The curly appearance, grading:

+++: very curly lock

++: moderately curly lock

+: slightly curly lock

−: non-curly lock

The tacky appearance of the lock, grading:

−: non-tacky appearance

+: tacky appearance

The following results were obtained:

|        | Curly appearance | Tacky appearance |
|--------|------------------|------------------|
| Lock 7 | ++               | −                |
| Lock 8 | −                | +                |
| Lock 9 | −                | +                |

The results obtained show that lock 7 treated with the process according to the invention has good curliness without a tacky feel.

EXAMPLE 8

The protocol similar to that described in example 8 was used, using the following compositions, respectively:
Composition 5: solution containing 5% of polymer from example 1 in cyclopentasiloxane
Composition 7: solution containing 35% by weight of polymer from example 3 in cyclopentasiloxane
Composition 5 and/or composition 7 were applied according to the following protocols:
Lock 10: treated with composition 5, then composition 7
Lock 11: treated just with composition 7.
The curly appearance of the treated lock and the tacky feel thereof were then observed, as described in example 8.
3 shampooing operations were then carried out according to the protocol described in example 6 and the curly appearance of the locks of hair was observed again.
The following results were obtained:

|         | Curly appearance | Tacky appearance | Curly appearance after 3 shampoo operations |
|---------|------------------|------------------|---------------------------------------------|
| Lock 10 | +++              | −                | Yes, curliness maintained                   |
| Lock 11 | +                | +                | No, curliness lost                          |

The results obtained show that lock 10 treated with the process according to the invention has good curliness without a tacky feel, with a persistent effect after 3 shampoo operations.

EXAMPLE 10

The protocol similar to that described in example 9 was used, using the following compositions, respectively:
Composition 8: solution containing 50% by weight of polymer from example 4 in water
Composition 7: solution containing 25% by weight of polymer from example 3 in cyclopentasiloxane
Composition 8 and/or composition 7 were applied according to the following protocols:
Lock 12: treated with composition 8, then composition 7
Lock 11: treated just with composition 7.
Lock 13: treated just with composition 8.
The following results were obtained:

|         | Curly appearance | Tacky appearance | Curly appearance after 3 shampoo operations |
|---------|------------------|------------------|---------------------------------------------|
| Lock 12 | +++              | −                | Yes                                         |
| Lock 11 | +                | +                | No                                          |
| Lock 13 | +                | −                | No                                          |

The results obtained show that lock 12 treated with the process according to the invention has good curliness without a tacky feel, with a persistent effect after 3 shampoo operations.

EXAMPLE 10

The following compositions were used:
Composition 7C: solution containing 50% by weight of polymer from example 3 in cyclopentasiloxane
Composition 4: solution containing 40% by weight of AM of the furfuryl compound (B) in cyclopentasiloxane
On an equivalent support of elastomer skin with a diameter of 4.5 cm, 1 ml of composition 7C was applied by spreading out with a brush, and was left to dry for 1 hour at room temperature (25° C.). 0.5 ml of composition 4 were then applied to the deposit of composition 7C, by spreading it out with a brush. The treated support was then placed in an oven at 37° C. for 1 hour. After drying, the formation of a non-tacky, transparent film was observed. 1 ml of an aqueous solution containing 5% by weight of sodium dodecyl sulfate was also applied to the film obtained, being left to act for 3 minutes;
it was observed that the film remains in a good state: it is therefore persistent with washing.

The invention claimed is:
1. A process for the cosmetic treatment of human keratin materials, comprising the following steps:
   a) a step of applying, to the keratin materials, a first cosmetic composition comprising a compound comprising at least 2 maleimide groups; and
   b) a step of applying a second cosmetic composition comprising a compound comprising at least 2 furfuryl groups.
2. The process according to claim 1, wherein the compound comprising at least 2 maleimide groups is chosen from:
   (a) the compounds of formula (I):

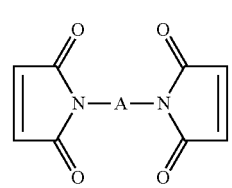

(I)

in which A denotes:
(i) a divalent hydrocarbon-based radical having from 3 to 20 carbon atoms, optionally substituted by one or more hydroxyl groups or by a maleimide group, optionally interrupted by an oxygen or sulfur atom or an —NR— group, R denoting a hydrogen atom or a $C_1$-$C_4$ alkyl radical or a —S(O)— or —SO$_2$— group; or
(ii) a polyethylene glycol and/or polypropylene glycol polymer chain; or
(iii) a silicone polymer chain,
(b) the polymer pentaerythritol tetra{[3-(3-maleimido-1-oxopropyl)amino]propyl}polyoxyethylene in which each polyoxyethylene segment comprises from 4 to 500 ethylene oxide units
(c) the maleimidoalkylmethylsiloxane-dimethylsiloxane copolymers of formula (II)

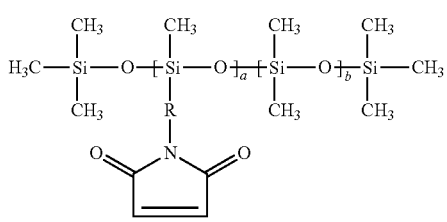

in which R denotes a divalent hydrocarbon-based radical having from 1 to 15 carbon atoms, optionally interrupted by one or more non-adjacent oxygen atom(s) or —NR'— groups, R' denoting H or a $C_1$-$C_4$ alkyl group;
a is a number ranging from 2 to 50;
b is a number ranging from 10 to 400;
(d) polymers of formula (III):

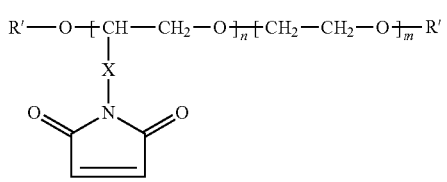

in which:
R' denotes a hydrogen atom or a $C_1$-$C_3$ alkyl group,
X denotes a divalent $C_1$-$C_{15}$ hydrocarbon-based group, optionally interrupted by one or more non-adjacent oxygen atom(s) or —NR'— groups, R' denoting H or a $C_1$-$C_4$ alkyl group;
n is an integer ranging from 3 to 20,
m+n is an integer ranging from 3 to 3000,
(e) the polymers of formula (IV):

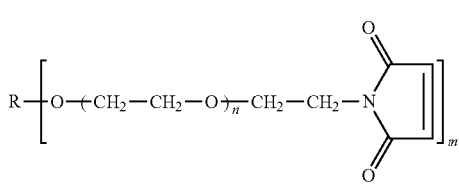

in which:
R denotes a multivalent radical derived from a $C_3$-$C_{12}$ polyol
n is an integer ranging from 3 to 3000,
m is an integer ranging from 3 to 12.

3. The process according to claim 1, wherein the compound with maleimide groups is chosen from:
1,2-bis(maleimido)ethane, 1,3-bis(maleimido)propane, 1,4-bis(maleimido)butane, 1,5-bis(maleimido)pentane, 1,5-bis(maleimido)-2-methylpentane, 1,6-bis(maleimido)hexane,
1,7-bis(maleimido)heptane, 1,8-bis(maleimido)octane, 1,10-bis(maleimido)decane, 1,4-bis(maleimido)-2,3-butanediol, bis(N-maleimidomethyl) ether,
1,11-bis(maleimido)tetraethyleneglycol, 1,8-bis(maleimido)triethyleneglycol, dithio-bis(maleimido)ethane, 1,13-bis(maleimido)-4,7,10-trioxatridecane, 1,1'-(3,6,9,12-tetraoxatetradecane-1,14-diyl)bis(1H-pyrrole-2,5-dione), 1,2-bis(maleimido)benzene, 1,3-bis(maleimido)benzene, 1,4-bis(maleimido)benzene, 2,4-bis(maleimido)toluene, 4,4'-bis(maleimido)diphenylmethane, 4,4'-bis(maleimido)-1,1'-biphenyl, 1,1'-[methylenebis(2-ethyl-6-methyl-4,1-phenylene)]bismaleimide, 2,2-bis[4-(4-maleimidophenoxy)phenyl] propane, 4,4'-bis(maleimido)diphenyl ether, 1,4-bis(4-maleimidophenoxy)benzene, 1,3-bis(4-maleimidophenoxy)benzene, 1,1'-[methylenebis(6-methoxy-3,1-phenylene)]bis 1H-pyrrole-2,5-dione, 1,1'-[1,4-phenylenebis[(1-oxo-2-propene-3,1-diyl)-3,1-phenylene]]bis-1H-pyrrole-2,5-dione, 4,4'-diphenyl sulfide bismaleimide,
bis[4-maleimido(4-phenoxyphenyl)] sulfone
bis(1,13-(3-malemidopropionyl)amido)-4,7,10-trioxatridecane and
tris(2-maleimidoehyl)amine.

4. The process according to claim 1, wherein the compound with maleimide groups is chosen from:
compounds of formula (I)

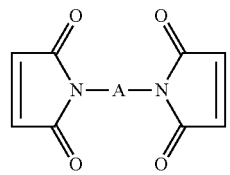

in which A denotes a divalent radical having from 3 to 6 carbon atoms, optionally substituted by one or more hydroxyl groups;
compounds of formula (Ia):

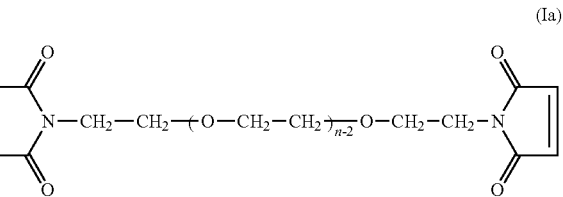

in which n is between 30 and 100;
compounds of formula (II):

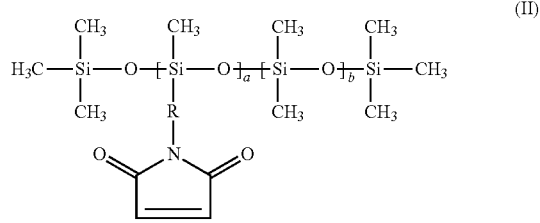

in which R denotes a divalent hydrocarbon-based radical having from 2 to 6 carbon atoms; a ranges from 2 to 10 and b ranges from 30 to 75.

5. The process according to claim 1, wherein the compound with maleimide groups is chosen from:
1,4-bis(maleimido)-2,3-butanediol;

compounds of formula (Ia):

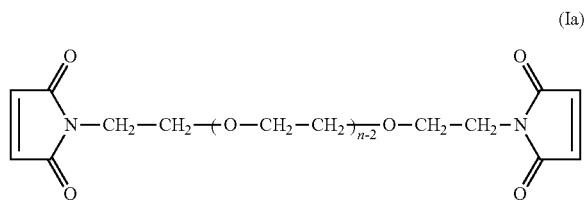

in which n is between 30 and 60;
compounds of formula (II):

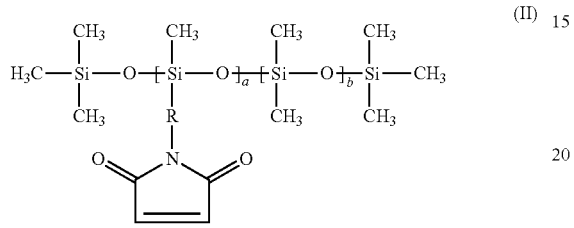

in which R denotes a divalent propylene radical; a ranges from 2 to 5 and b ranges from 40 to 70.

6. The process according to claim 1, wherein the compound with maleimide groups is present in the first composition in a content ranging from 0.1% to 40% by weight, relative to the total weight of the composition.

7. The process according to claim 1, wherein the compound with furfuryl groups is a compound of formula (V):

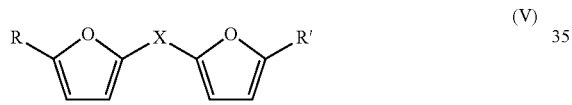

in which:
X denotes:
(i) a divalent —C($R_1$)($R_2$)— group, with $R_1$ and $R_2$ denoting a $C_1$-$C_4$ alkyl radical; or $R_1$=H and $R_2$ denotes a $C_1$-$C_4$ alkyl group, or —OH or NH$R_3$, with $R_3$=$C_1$-$C_4$ alkyl radical;
(ii) a sulfur atom;
(iii) a —CO— group;
(iv) an —Si($R_4$)($R_5$) group, $R_4$ and $R_5$ denoting a $C_1$-$C_4$ alkyl radical,
R and R' denote a $C_1$-$C_4$ alkyl radical or a —CHO aldehyde group.

8. The process according to claim 1, wherein the compound with furfuryl groups is chosen from:
bis(2-furylmethoxy)(dimethyl) silane
di-2-furanyl methanone
bis-furan-2,2'-(1-methylethylidene)
bis(5-methyl-2-furyl) ketone
alpha-2-furanyl-2-furanemethanamine
5,5'-thiobis 2-furan carboxaldehyde
alpha-2-furanyl-2-furanmethanol
5,5'-(1-Methylethylidene)bis-2-furan carboxaldehyde
N-ethyl-5-methyl-alpha-(5-methyl-2-furanyl)-2-furanmethanamine
2,2''methylene bis-furan and
di-2-furanyldimethyl silane.

9. The process according to claim 1, wherein the compound with furfuryl groups is bis(2-furylmethoxy)(dimethyl)silane.

10. The process according to claim 1, wherein the compound with furfuryl groups is chosen from:
copolymers of 4-furfuryloxymethylstyrene and styrene;
furan-modified poly(2-methyl-2-oxazolines);
furan-modified poly(N-acetylthylenimines);
copolymers of furfuryl methacrylate and styrene; and
polyamides with furan function.

11. The process according to claim 1, wherein the compound with furfuryl groups is a copolymer resulting from the polymerization of:
i) furfuryl methacrylate;
ii) (meth)acrylamides of formula $CH_2$=C(R1)—CONR'$_3$R'$_4$, in which:
R1 denotes H or methyl;
R'3 and R'4, which are identical or different, represent a hydrogen atom or a linear or branched alkyl group comprising from 1 to 6 carbon atoms, which optionally comprises one or more substituents chosen from —OH, =O, halogen atoms and —NR'R" with R' and R", which are identical or different, chosen from linear or branched $C_1$-$C_4$ alkyls; or
R'3 represents a hydrogen atom and R'4 represents a 1,1-dimethyl-3-oxobutyl group;
iii) an additional monomer chosen from:
a) the monomers of formula (VI), alone or as a mixture:

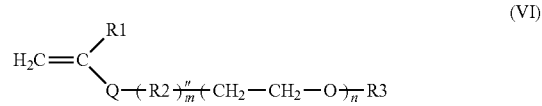

in which:
$R_1$ is a hydrogen atom or a methyl radical;
Q is a divalent group chosen from —COO—, —CONH—,
$R_2$ is a linear, branched or cyclic, saturated or unsaturated, optionally aromatic divalent carbon-based radical, comprising 1 to 18 carbon atoms, which optionally comprises 1 to 4 non-adjacent heteroatoms chosen from O or S or an —NR'— group, R' denoting H or a $C_1$-$C_4$ alkyl group,
m is 0 or 1
n is an integer between 65 and 700;
$R_3$ is a hydrogen atom or a linear, branched or cyclic, saturated or unsaturated, optionally aromatic carbon-based radical, comprising 1 to 30 carbon atoms, which optionally comprises 1 to 4 non-adjacent heteroatoms chosen from O or S or an —NR'— group, R' denoting H or a $C_1$-$C_4$ alkyl group,
b) a polydimethylsiloxane monomer with mono(meth)acryloyloxy end group of the following formula (VII'):

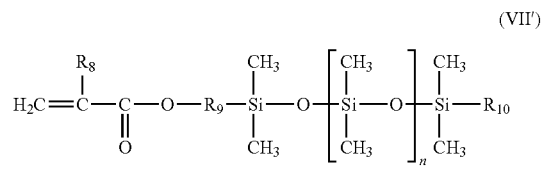

in which:
$R_8$ denotes a hydrogen atom or a methyl group;
$R_9$ denotes a linear divalent hydrocarbon-based group having from 2 to 4 carbon atoms;

$R_{10}$ denotes an alkyl group chosen from methyl, ethyl, propyl, butyl or pentyl;

n denotes an integer ranging from 1 to 300

(iii) and optionally an alkyl (meth)acrylate chosen from:

(a) linear or branched, saturated or unsaturated $C_1$-$C_{20}$ alkyl (meth)acrylates, optionally interrupted by one or more non-adjacent heteroatoms chosen from O and S or by an NR group, R being a $C_1$-$C_4$ alkyl group, optionally substituted by a phenyl or furfuryl group;

(b) saturated $C_4$-$C_8$ cycloalkyl (meth)acrylates optionally interrupted by O or NH.

12. The process according to claim 1, wherein the compound with furfuryl groups is a copolymer resulting from the polymerization of:

i) furfuryl methacrylate;

ii) (meth)acrylamide of formula $CH_2=C(R1)-CONR'_3R'_4$, in which:

$R_1$ denotes H or methyl;

$R'_3$ and $R'_4$, which are identical or different, represent a hydrogen atom or a linear or branched alkyl group comprising from 1 to 6 carbon atoms, which optionally comprises an —NR'R" substituent, with R' and R", which are identical or different, chosen from linear or branched $C_1$-$C_4$ alkyls;

iii) additional monomer chosen from:

a) the monomers of formula (VI'), alone or as a mixture:

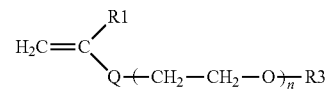

(VI')

in which:

$R_1$ is a hydrogen atom or a methyl radical;

Q is a divalent group —COO—, n is an integer between 65 and 700;

$R_3$ is a hydrogen atom or a methyl radical b) a polydimethylsiloxane monomer with mono(meth)acryloyloxy end group of the following formula (VII'):

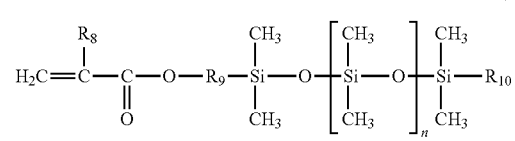

(VII')

in which:

$R_8$ denotes a hydrogen atom or a methyl group;

$R_9$ denotes a linear divalent hydrocarbon-based group having from 2 to 4 carbon atoms;

$R_{10}$ denotes an alkyl group chosen from methyl, ethyl, propyl, butyl or pentyl;

n denotes an integer ranging from 1 to 300 iv) and optionally a $C_1$-$C_{20}$ alkyl (meth)acrylate monomer.

13. The process according to claim 1, wherein the compound with furfuryl groups is a copolymer resulting from the polymerization of:

i) furfuryl methacrylate;

ii) dimethylaminopropyl methacrylamide iii) additional monomer chosen from:

a) the monomers of formula (VI'), alone or as a mixture:

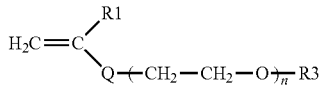

(VI')

in which:

$R_1$ is a hydrogen atom or a methyl radical;

Q is a divalent group —COO—, n is an integer between 100 and 200;

$R_3$ is a hydrogen atom or a methyl radical;

b) a polydimethylsiloxane monomer with mono(meth)acryloyloxy end group of the following formula (VII'):

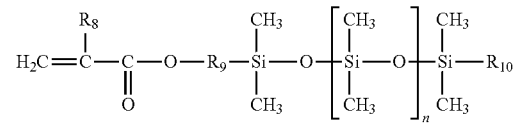

(VII')

in which:

$R_8$ denotes a methyl group;

$R_9$ denotes a linear divalent hydrocarbon-based group having from 2 to 4 carbon atoms;

$R_{10}$ denotes an alkyl group chosen from methyl, ethyl, propyl, butyl or pentyl;

n denotes an integer ranging from 5 to 100;

iv) and optionally a $C_1$-$C_{20}$ alkyl (meth)acrylate monomer.

14. The process according to claim 11, wherein the furfuryl copolymer is obtained from said monomers in the following contents by weight relative to the total weight of monomers used:

from 1% to 50% by weight of furfuryl (meth)acrylate;

from 1% to 90% by weight of (meth)acrylamide type monomer;

from 1% to 90% by weight of additional monomer (VI), (VI') or (VII), (VII');

and, if present, from 1% to 90% by weight of $C_1$-$C_{20}$ alkyl (meth)acrylate.

15. The process according to claim 11, wherein the furfuryl copolymer is obtained from said monomers in the following contents by weight relative to the total weight of monomers used:

from 5% to 45% by weight of furfuryl (meth)acrylate;

from 5% to 50% by weight of (meth)acrylamide type monomer;

from 5% to 50% by weight of additional monomer (VI), (VI') or (VII), (VII');

and, if present, from 5% to 50% by weight of $C_1$-$C_{20}$ alkyl (meth)acrylate.

16. The process according to claim 11, wherein the polymer comprises said (meth)acrylamide monomer with at least said —NR'R" group and is neutralized with an inorganic or organic acid.

17. The process according to claim 11, wherein the compound with furfuryl group is chosen from:

polyethylene glycol methacrylate/dimethylaminopropyl methacrylamide/furfuryl methacrylate copolymer 2-ethylhexyl acrylate/dimethylaminopropyl methacrylamide/furfuryl methacrylate/PDMS acrylate copolymer 2-ethylhexyl acrylate/furfuryl methacrylate/PDMS acrylate copolymer
the PDMS acrylate being of formula:

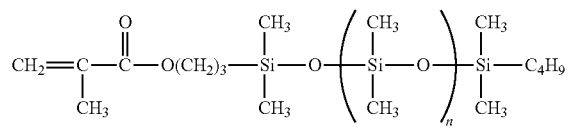

n being between 60 and 70.

18. The process according to claim 1, wherein the compound with furfuryl groups is present in the second composition in a content ranging from 0.1% to 30% by weight, relative to the total weight of the composition.

19. The process according to claim 1, which is performed by carrying out, in order, step a) then step b).

20. The process according to claim 1, which is performed by carrying out, in order, step b) then step a).

21. The process according to claim 1, wherein the second step is carried out in a period of time from 1 second to 1 hour after having carried out the first step.

22. The process according to claim 1, wherein the composition containing the compound with furfuryl groups or the compound with maleimide groups having the highest molecular weight is applied in the first step, then in the second step the composition containing the compound with furfuryl groups or the compound with maleimide groups having the lowest molecular weight is applied.

23. The process according to claim 1, wherein the first and second compositions are extemporaneously mixed, then the mixture obtained is applied to the keratin materials in a period of time of less than or equal to approximately 30 minutes after formation of the mixture.

24. The process according to claim 1, wherein the compound with maleimide groups and the compound with furfuryl groups are used in amounts such that the mole ratio of the number of maleimide groups relative to the number of furfuryl groups is between 0.95 and 1.05.

25. The process according to claim 1, wherein the human keratin materials are chosen from the skin, the lips, the hair, the eyelashes, and the nails.

26. The process according to claim 1, wherein the human keratin materials are hair.

* * * * *